US 8,206,635 B2

(12) United States Patent
Ramzipoor et al.

(10) Patent No.: US 8,206,635 B2
(45) Date of Patent: Jun. 26, 2012

(54) STENT FABRICATION VIA TUBULAR CASTING PROCESSES

(75) Inventors: Kamal Ramzipoor, Fremont, CA (US); Alfred N. K. Chia, Singapore (SG); Liwei Wang, Singapore (SG)

(73) Assignee: Amaranth Medical Pte., Singapore (SG)

( * ) Notice: Subject to any disclaimer, the term of this patent is extended or adjusted under 35 U.S.C. 154(b) by 466 days.

(21) Appl. No.: 12/143,659

(22) Filed: Jun. 20, 2008

(65) Prior Publication Data

US 2009/0319028 A1 Dec. 24, 2009

(51) Int. Cl.
*B28B 5/02* (2006.01)
*B29C 43/22* (2006.01)
*B29D 22/00* (2006.01)
*A61K 49/04* (2006.01)
*A61K 31/727* (2006.01)
*A61F 2/00* (2006.01)

(52) U.S. Cl. ........ 264/294; 264/503; 264/573; 424/426; 424/9.41; 514/56

(58) Field of Classification Search .................. 264/294, 264/503, 573; 424/426, 9.41; 514/56
See application file for complete search history.

(56) References Cited

U.S. PATENT DOCUMENTS

| | | | |
|---|---|---|---|
| 4,173,689 | A | 11/1979 | Lyman et al. |
| 4,334,327 | A | 6/1982 | Lyman et al. |
| 4,661,530 | A | 4/1987 | Gogolewski et al. |
| 4,770,664 | A | 9/1988 | Gogolewski |
| 4,834,747 | A | 5/1989 | Gogolewski |
| 4,955,899 | A | 9/1990 | Della Corna et al. |
| 5,104,400 | A | 4/1992 | Berguer et al. |
| 5,152,782 | A | 10/1992 | Kowligi et al. |
| 5,670,161 | A | 9/1997 | Healy et al. |
| 5,935,164 | A | 8/1999 | Iversen |
| 5,935,506 | A | 8/1999 | Schmitz et al. |
| 6,090,134 | A | 7/2000 | Tu et al. |
| 6,153,252 | A | 11/2000 | Hossainy et al. |

(Continued)

FOREIGN PATENT DOCUMENTS

WO WO 2009/155560 12/2009

OTHER PUBLICATIONS

PCT International Patent Application No. PCT/US2009/048030 filed Jun. 19. 2009 in the name of Ramzipoor et al., International Search Report and Written Opinion mailed Aug. 7, 2009.

(Continued)

*Primary Examiner* — Christina Johnson
*Assistant Examiner* — Michael Piery
(74) *Attorney, Agent, or Firm* — Levine Bagade Han LLP

(57) ABSTRACT

Tubular casting processes, such as dip-coating, may be used to form substrates from polymeric solutions which may be used to fabricate implantable devices such as stents. The polymeric substrates may have multiple layers which retain the inherent properties of their starting materials and which are sufficiently ductile to prevent brittle fracture. Parameters such as the number of times the mandrel is immersed, the duration of time of each immersion within the solution, as well as the delay time between each immersion or the drying or curing time between dips and withdrawal rates of the mandrel from the solution may each be controlled to result in the desired mechanical characteristics. Additional post-processing may also be utilized to further increase strength of the substrate or to alter its shape.

74 Claims, 12 Drawing Sheets

U.S. PATENT DOCUMENTS

| | | |
|---|---|---|
| 6,217,815 B1 | 4/2001 | Sisbarro |
| 6,231,326 B1 | 5/2001 | Sisbarro |
| 6,322,847 B1 | 11/2001 | Zhong et al. |
| 6,635,082 B1 | 10/2003 | Hossainy et al. |
| 6,833,153 B1 | 12/2004 | Roorda et al. |
| 6,860,946 B2 | 3/2005 | Hossainy et al. |
| 6,866,805 B2 | 3/2005 | Hong et al. |
| 6,989,071 B2 | 1/2006 | Kocur et al. |
| 7,112,298 B2 | 9/2006 | Kampa et al. |
| 7,311,727 B2 | 12/2007 | Mazumder et al. |
| 2003/0050687 A1 | 3/2003 | Schwade et al. |
| 2003/0060836 A1 | 3/2003 | Wang et al. |
| 2003/0157241 A1 | 8/2003 | Hossainy et al. |
| 2003/0195628 A1 | 10/2003 | Bao et al. |
| 2003/0225447 A1 | 12/2003 | Majercak et al. |
| 2004/0030377 A1 | 2/2004 | Dubson et al. |
| 2004/0113306 A1 | 6/2004 | Rapacki et al. |
| 2004/0127932 A1 | 7/2004 | Shah |
| 2004/0127970 A1 | 7/2004 | Saunders et al. |
| 2004/0164030 A1 | 8/2004 | Lowe et al. |
| 2005/0187608 A1 | 8/2005 | O'Hara |
| 2006/0025852 A1 | 2/2006 | Armstrong et al. |
| 2006/0122686 A1 | 6/2006 | Gilad et al. |
| 2006/0142736 A1* | 6/2006 | Hissink et al. ............ 604/540 |
| 2006/0149365 A1 | 7/2006 | Fifer et al. |
| 2006/0212064 A1 | 9/2006 | Shah |
| 2006/0259133 A1 | 11/2006 | Sowinski et al. |
| 2006/0287715 A1 | 12/2006 | Atladottir et al. |
| 2007/0038290 A1 | 2/2007 | Huang et al. |
| 2007/0100430 A1 | 5/2007 | Rudakov et al. |
| 2007/0106361 A1 | 5/2007 | Epstein |
| 2007/0110889 A1 | 5/2007 | Sundar |
| 2007/0185561 A1 | 8/2007 | Schmitz et al. |
| 2007/0202046 A1* | 8/2007 | Dave ........................ 424/9.41 |
| 2007/0250153 A1 | 10/2007 | Cully et al. |
| 2007/0281117 A1 | 12/2007 | Kaplan et al. |
| 2007/0283552 A1* | 12/2007 | Gale et al. ................... 29/515 |
| 2008/0051866 A1 | 2/2008 | Chen et al. |
| 2008/0091275 A1 | 4/2008 | Ducharme |
| 2008/0103584 A1 | 5/2008 | Su et al. |
| 2010/0004734 A1 | 1/2010 | Ramzipoor et al. |

OTHER PUBLICATIONS

PCT International Patent Application No. PCT/US2009/048030 filed Jun. 19, 2009 in the name of Ramzipoor et al., International Preliminary Report on Patentability mailed Jan. 6, 2011.

* cited by examiner

STENT FABRICATION VIA TUBULAR CASTING PROCESSES

FIELD OF THE INVENTION

The present invention relates generally to manufacturing processes for forming or creating devices which are implantable within a patient, such as medical devices. More particularly, the present invention relates to methods and processes for forming or creating tubular substrates which may be further processed to create medical devices having various geometries suitable for implantation within a patient.

BACKGROUND OF THE INVENTION

In recent years there has been growing interest in the use of artificial materials, particularly materials formed from polymers, for use in implantable devices that come into contact with bodily tissues or fluids particularly blood. Some examples of such devices are artificial heart valves, stents, and vascular prosthesis. Some medical devices such as implantable stents which are fabricated from a metal have been problematic in fracturing or failing after implantation. Moreover, certain other implantable devices made from polymers have exhibited problems such as increased wall thickness to prevent or inhibit fracture or failure. However, stents having reduced wall thickness are desirable particularly for treating arterial diseases.

Because many polymeric implants such as stents are fabricated through processes such as extrusion or injection molding, such methods typically begin the process by starting with an inherently weak material. In the example of a polymeric stent, the resulting stent may have imprecise geometric tolerances as well as reduced wall thicknesses which may make these stents susceptible to brittle fracture.

A stent which is susceptible to brittle fracture is generally undesirable because of its limited ability to collapse for intravascular delivery as well as its limited ability to expand for placement or positioning within a vessel. Moreover, such polymeric stents also exhibit a reduced level of strength. Brittle fracture is particularly problematic in stents as placement of a stent onto a delivery balloon or within a delivery sheath imparts a substantial amount of compressive force in the material comprising the stent. A stent made of a brittle material may crack or have a very limited ability to collapse or expand without failure. Thus, a certain degree of malleability is desirable for a stent to expand, deform, and maintain its position securely within the vessel.

Accordingly, it is desirable to produce a polymeric substrate having one or more layers which retains its mechanical strength and is sufficiently ductile so as to prevent or inhibit brittle fracture, particularly when utilized as a biocompatible and/or bioabsorbable polymeric stent for implantation within a patient body.

SUMMARY OF THE INVENTION

A number of casting processes described herein may be utilized to develop substrates, e.g., cylindrically shaped substrates, having a relatively high level of geometric precision and mechanical strength. These polymeric substrates can then be machined using any number of processes (e.g., high-speed laser sources, mechanical machining, etc.) to create devices such as stents having a variety of geometries for implantation within a patient, such as the peripheral or coronary vasculature, etc.

An example of such a casting process is to utilize a dip-coating process. The utilization of dip-coating to create a polymeric substrate having such desirable characteristics results in substrates which are able to retain the inherent properties of the starting materials. This in turn results in substrates having a relatively high radial strength which is retained through any additional manufacturing processes for implantation. Additionally, dip-coating the polymeric substrate also allows for the creation of substrates having multiple layers.

The molecular weight of a polymer is typically one of the factors in determining the mechanical behavior of the polymer. With an increase in the molecular weight of a polymer, there is generally a transition from brittle to ductile failure. A mandrel may be utilized to cast or dip-coat the polymeric substrate.

In dip-coating the polymeric substrate, one or more high molecular weight biocompatible and/or bioabsorbable polymers may be selected for forming upon the mandrel. The one or more polymers may be dissolved in a compatible solvent in one or more corresponding containers such that the appropriate solution may be placed under the mandrel. As the substrate may be formed to have one or more layers overlaid upon one another, the substrate may be formed to have a first layer of a first polymer, a second layer of a second polymer, and so on depending upon the desired structure and properties of the substrate. Thus, the various solutions and containers may be replaced beneath the mandrel between dip-coating operations in accordance with the desired layers to be formed upon the substrate such that the mandrel may be dipped sequentially into the appropriate polymeric solution.

Parameters such as the number of times the mandrel is immersed, the sequence and direction of dipping, the duration of time of each immersion within the solution, as well as the delay time between each immersion or the drying or curing time between dips and dipping and/or withdrawal rates of the mandrel to and/or from the solution may each be controlled to result in the desired mechanical characteristics. Formation via the dip-coating process may result in a polymeric substrate having half the wall thickness while retaining an increased level of strength in the substrate as compared to an extruded polymeric structure.

The immersion times as well as drying times may be uniform between each immersion or they may be varied as determined by the desired properties of the resulting substrate. Moreover, the substrate may be placed in an oven or dried at ambient temperature between each immersion or after the final immersion to attain a predetermined level of crystals, e.g., 60%, and a level of amorphous polymeric structure, e.g., 40%. Each of the layers overlaid upon one another during the dip-coating process are tightly adhered to one another and the wall thicknesses and mechanical properties of each polymer are retained in their respective layer with no limitation on the molecular weight and/or crystalline structure of the polymers utilized.

Dip-coating can be used to impart an orientation between layers (e.g., linear orientation by dipping; radial orientation by spinning the mandrel; etc.) to further enhance the mechanical properties of the formed substrate. As radial strength is a desirable attribute of stent design, post-processing of the formed substrate may be accomplished to impart such attributes. Typically, polymeric stents suffer from having relatively thick walls to compensate for the lack of radial strength, and this in turn reduces flexibility, impedes navigation, and reduces arterial luminal area immediately post implantation. Post-processing may also help to prevent material creep and recoil (creep is a time-dependent permanent deformation that occurs to a specimen under stress, typically under elevated temperatures) which are problems typically associated with polymeric stents.

For post-processing, a predetermined amount of force may be applied to the substrate where such a force may be generated by a number of different methods. One method is by utilizing an expandable pressure vessel placed within the substrate. Another method is by utilizing a braid structure, such as a braid made from a super-elastic or shape memory alloy like NiTi alloy, to increase in size and to apply the desirable degree of force against the interior surface of the substrate.

Yet another method may apply the expansion force by application of a pressurized inert gas such as nitrogen within the substrate lumen. A completed substrate may be placed inside a molding tube which has an inner diameter that is larger than the cast cylinder. A distal end or distal portion of the cast cylinder may be clamped or otherwise closed and a pressure source may be coupled to a proximal end of the cast cylinder. The entire assembly may be positioned over a nozzle which applies heat to either the length of the cast cylinder or to a portion of cast cylinder. The increase in diameter of the cast cylinder may thus realign the molecular orientation of the cast cylinder to increase its radial strength. After the diameter has been increased, the cast cylinder may be cooled.

Once the processing has been completed on the polymeric substrate, the substrate may be further formed or machined to create a variety of device. One example includes stents created from the cast cylinder by cutting along a length of the cylinder to create a rolled stent for delivery and deployment within the patient vasculature. Another example includes machining a number of portions to create a lattice or scaffold structure which facilitates the compression and expansion of the stent.

In other variations, in forming the stent, the substrate may be first formed at a first diameter, as described herein by immersing a mandrel into at least a first polymeric solution such that at least a first layer of a biocompatible polymer substrate is formed upon the mandrel and has a first diameter defined by the mandrel. In forming the substrate, parameters such as controlling a number of immersions of the mandrel into the first polymeric solution, controlling a duration of time of each immersion of the mandrel, and controlling a delay time between each immersion of the mandrel are controlled. With the substrate initially formed, the first diameter of the substrate may be reduced to a second smaller diameter and processed to form an expandable stent scaffold configured for delivery and deployment within a vessel, wherein the stent scaffold retains one or more mechanical properties of the polymer resin such that the stent scaffold exhibits ductility upon application of a load.

With the stent scaffold formed and heat set to have an initial diameter, it may be reduced to a second delivery diameter and placed upon a delivery catheter for intravascular delivery within a patient body comprising positioning the stent having the second diameter at a target location within the vessel, expanding the stent to a third diameter that is larger than the second diameter (and possibly smaller than the initial diameter) at the target location utilizing an inflation balloon or other mechanism, and allowing the stent to then self-expand into further contact with the vessel at the target location such that the stent self-expands over time back to its initial diameter or until it is constrained from further expansion by the vessel walls.

DETAILED DESCRIPTION OF THE INVENTION

Figure 1:
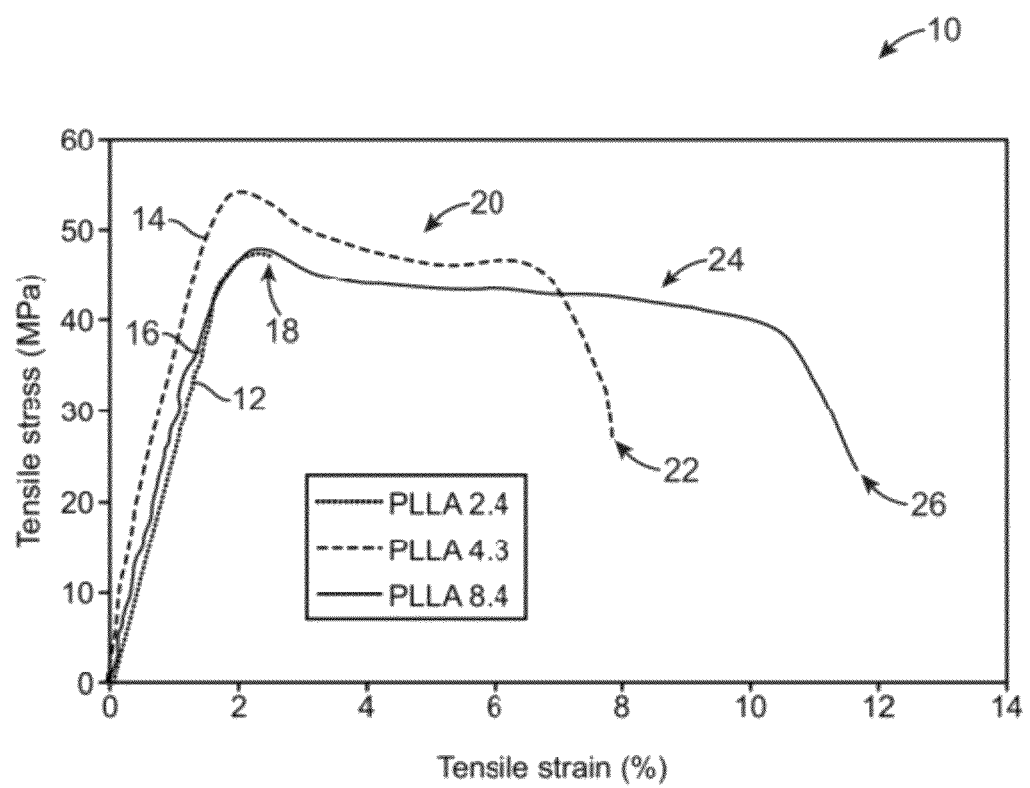
FIG. 1 illustrates a stress-strain plot of polylactic acid (PLLA) at differing molecular weights and their corresponding stress-strain values indicating brittle fracture to ductile failure.

In manufacturing implantable devices from polymeric materials such as biocompatible and/or biodegradable polymers, a number of casting processes described herein may be utilized to develop substrates, e.g., cylindrically shaped substrates, having a relatively high level of geometric precision and mechanical strength. These polymeric substrates can then be machined using any number of processes (e.g., high-speed laser sources, mechanical machining, etc.) to create devices such as stents having a variety of geometries for implantation within a patient, such as the peripheral or coronary vasculature, etc.

An example of such a casting process is to utilize a dip-coating process. The utilization of dip-coating to create a polymeric substrate having such desirable characteristics results in substrates which are able to retain the inherent properties of the starting materials. This in turn results in substrates having a relatively high radial strength which is mostly retained through any additional manufacturing processes for implantation. Additionally, dip-coating the polymeric substrate also allows for the creation of substrates having multiple layers. The multiple layers may be formed from the same or similar materials or they may be varied to include any number of additional agents, such as one or more drugs for treatment of the vessel, as described in further detail below. Moreover, the variability of utilizing multiple layers for the substrate may allow one to control other parameters, conditions, or ranges between individual layers such as varying the degradation rate between layers while maintaining the intrinsic molecular weight and mechanical strength of the polymer at a high level with minimal degradation of the starting materials.

Because of the retention of molecular weight and mechanical strength of the starting materials via the casting or dip-coating process, polymeric substrates may be formed which enable the fabrication of devices such as stents with reduced wall thickness which is highly desirable for the treatment of arterial diseases. Furthermore these processes may produce structures having precise geometric tolerances with respect to wall thicknesses, concentricity, diameter, etc.

One mechanical property in particular which is generally problematic with, e.g., polymeric stents formed from polymeric substrates, is failure via brittle fracture of the device when placed under stress within the patient body. It is generally desirable for polymeric stents to exhibit ductile failure under an applied load rather via brittle failure, especially during delivery and deployment of a polymeric stent from an inflation balloon or constraining sheath, as mentioned above. Percent (%) ductility is generally a measure of the degree of plastic deformation that has been sustained by the material at fracture. A material that experiences very little or no plastic deformation upon fracture is brittle.

The molecular weight of a polymer is typically one of the factors in determining the mechanical behavior of the polymer. With an increase in the molecular weight of a polymer, there is generally a transition from brittle to ductile failure. An example is illustrated in the stress-strain plot 10 which illustrate the differing mechanical behavior resulting from an increase in molecular weight. The stress-strain curve 12 of a sample of polylactic acid (PLLA) 2.4 shows a failure point 18 having a relatively low tensile strain percentage at a high tensile stress level indicating brittle failure. A sample of PLLA 4.3, which has a relatively higher molecular weight than PLLA 2.4, illustrates a stress-strain curve 14 which has a region of plastic failure 20 after the onset of yielding and a failure point 22 which has a relatively lower tensile stress value at a relatively higher tensile strain percentage indicating a degree of ductility. Yield occurs when a material initially departs from the linearity of a stress-strain curve and experiences an elastic-plastic transition.

A sample of PLLA 8.4, which has yet a higher molecular weight than PLLA 4.3, illustrates a stress-strain curve 16 which has a longer region of plastic failure 24 after the onset of yielding. The failure point 26 also has a relatively lower tensile stress value at a relatively higher tensile strain percentage indicating a degree of ductility. Thus, a high-strength tubular material which exhibits a relatively high degree of ductility may be fabricated utilizing polymers having a relatively high molecular weight (e.g., PLLA 8.4, PLLA with 8.28 IV, etc.). Such a tubular material may be processed via any number of machining processes to form an implantable device such as a stent which exhibits a stress-strain curve which is associated with the casting or dip-coating process described herein.

Figure 2A:
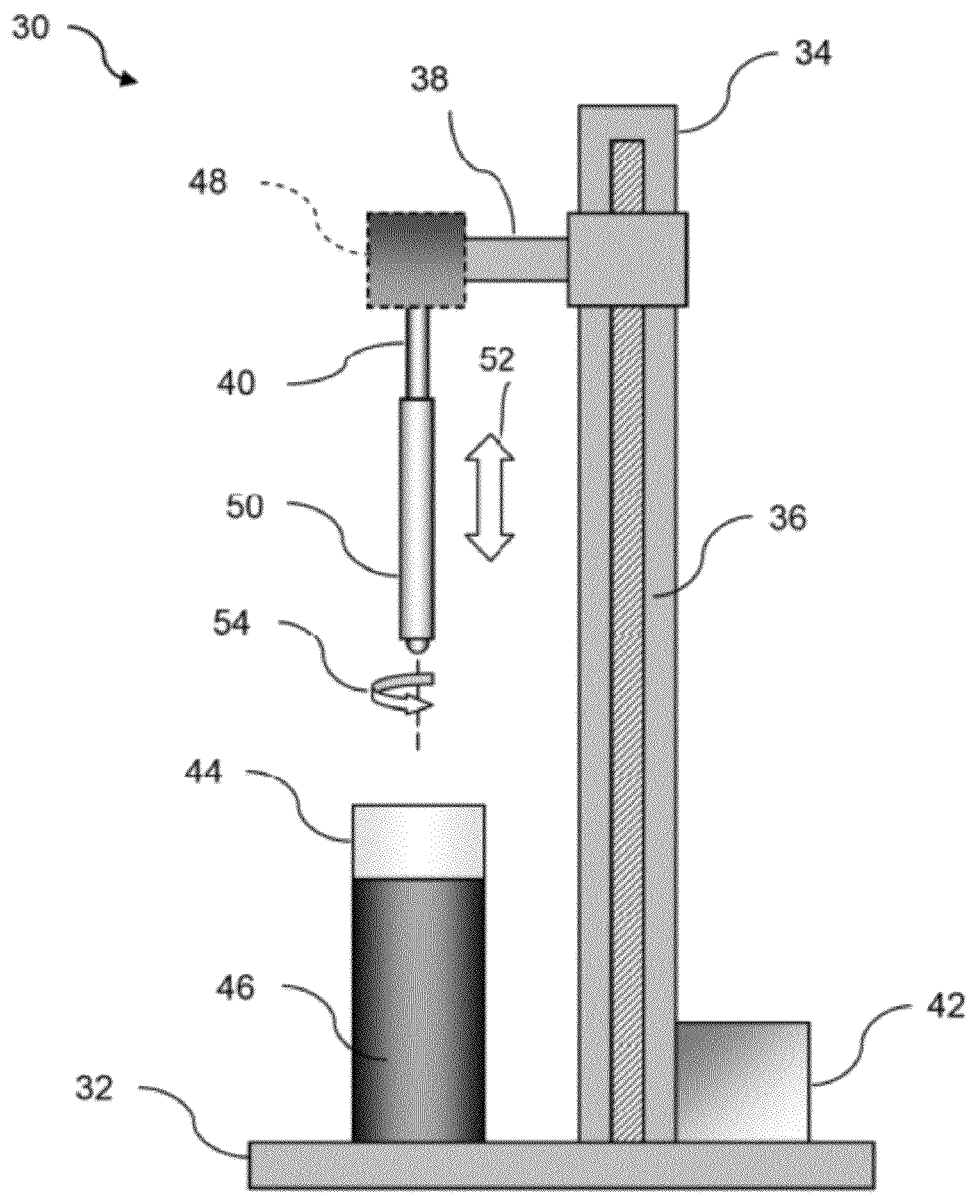
FIG. 2A illustrates an example of a dip-coating machine which may be utilized to form a polymeric substrate having one or more layers formed along a mandrel.

An example of a mandrel which may be utilized to cast or dip-coat the polymeric substrate is illustrated in the side view of FIG. 2A. Generally, dip coating assembly 30 may be any structure which supports the manufacture of the polymeric substrate in accordance with the description herein. A base 32 may support a column 34 which houses a drive column 36 and a bracket arm 38. Motor 42 may urge drive column 36 vertically along column 34 to move bracket arm 38 accordingly. Mandrel 40 may be attached to bracket arm 38 above container 44 which may be filled with a polymeric solution 46 (e.g., PLLA, PLA, PLGA, etc.) into which mandrel 40 may be dipped via a linear motion 52. The one or more polymers may be dissolved in a compatible solvent in one or more corresponding containers 44 such that the appropriate solution may be placed under mandrel 40. An optional motor 48 may be mounted along bracket arm 38 or elsewhere along assembly 30 to impart an optional rotational motion 54 to mandrel 40 and the substrate 50 formed along mandrel 40 to impart an increase in the circumferential strength of substrate 50 during the dip-coating process, as described in further detail below.

The assembly 30 may be isolated on a vibration-damping or vibrationally isolated table to ensure that the liquid surface held within container 44 remains completely undisturbed to facilitate the formation of a uniform thickness of polymer material along mandrel 40 and/or substrate 50 with each deposition The entire assembly 30 or just a portion of the assembly such as the mandrel 40 and polymer solution may be placed in an inert environment such as a nitrogen gas environment while maintaining a very low relative humidity (RH) level, e.g., less than 30% RH, and appropriate dipping temperature, e.g., at least 20° C. below the boiling point of the solvent within container 44 so as to ensure adequate bonding between layers of the dip-coated substrate. Multiple mandrels may also be mounted along bracket arm 38 or directly to column 34.

The mandrel 40 may be sized appropriately and define a cross-sectional geometry to impart a desired shape and size to the substrate 50. Mandrel 40 may be generally circular in cross section although geometries may be utilized as desired. In one example, mandrel 40 may define a circular geometry having a diameter ranging from 1 mm to 20 mm to form a polymeric substrate having a corresponding inner diameter. Moreover, mandrel 40 may be made generally from various materials which are suitable to withstand dip-coating processes, e.g., stainless steel, copper, aluminum, silver, brass, nickel, titanium, etc. The length of mandrel 40 that is dipped into the polymer solution may be optionally limited in length by, e.g., 50 cm, to ensure that an even coat of polymer is formed along the dipped length of mandrel 40 to limit the effects of gravity during the coating process. Mandrel 40 may also be made from a polymeric material which is lubricious, strong, has good dimensional stability, and is chemically resistant to the polymer solution utilized for dip-coating, e.g., fluoropolymers, polyacetal, polyester, polyamide, polyacrylates, etc.

Moreover, mandrel 40 may be made to have a smooth surface for the polymeric solution to form upon. In other variations, mandrel 40 may define a surface that is coated with a material such as polytetrafluroethylene to enhance removal of the polymeric substrate formed thereon. In yet other variations, mandrel 40 may be configured to define any number of patterns over its surface, e.g., either over its entire length or just a portion of its surface, that can be mold-transferred during the dip-coating process to the inner surface of the first layer of coating of the dip-coated substrate tube. The patterns may form raised or depressed sections to form various patterns such as checkered, cross-hatched, cratered, etc. that may enhance endothelialization with the surrounding tissue after the device is implanted within a patient, e.g., within three months or of implantation.

The direction that mandrel 40 is dipped within polymeric solution 46 may also be alternated or changed between layers of substrate 50. In forming substrates having a length ranging from, e.g., 1 cm to 40 cm or longer, substrate 50 may be removed from mandrel 40 and replaced onto mandrel 40 in an opposite direction before the dipping process is continued. Alternatively, mandrel 40 may be angled relative to bracket arm 38 and/or polymeric solution 46 during or prior to the dipping process.

Figure 2B:
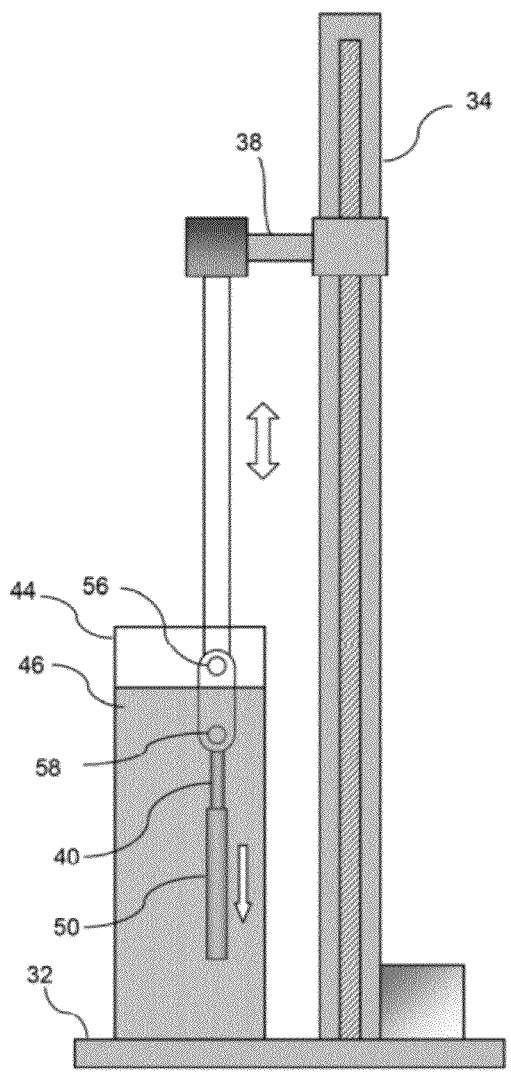
FIGS. 2B and 2C illustrate another example of a dip-coating assembly having one or more articulatable linkages to adjust a dipping direction of the mandrel.
Figure 2C:
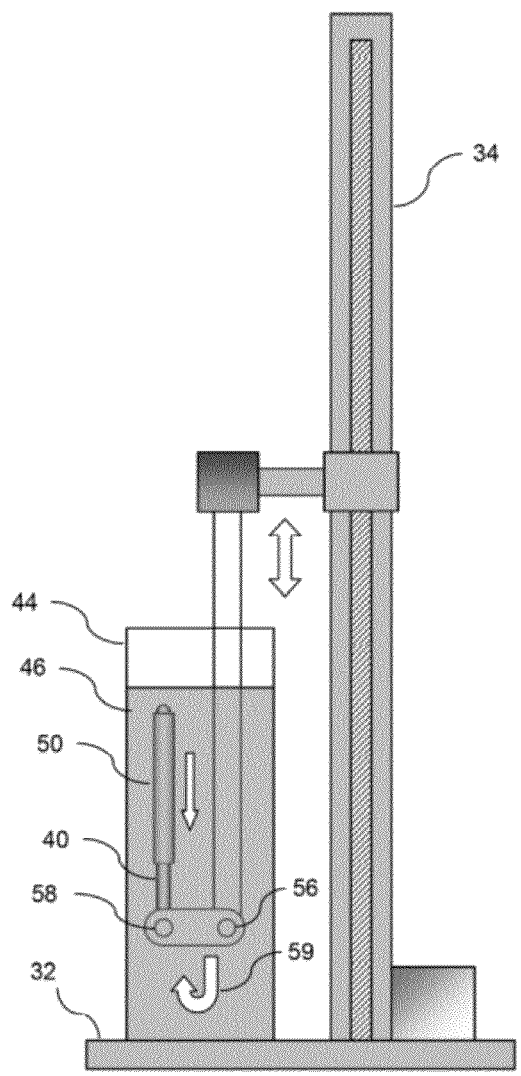

This may also be accomplished in yet another variation by utilizing a dipping assembly as illustrated in FIGS. 2B and 2C to achieve a uniform wall thickness throughout the length of the formed substrate 50 per dip. For instance, after 1 to 3 coats are formed in a first dipping direction, additional layers formed upon the initial layers may be formed by dipping mandrel 40 in a second direction opposite to the first dipping direction, e.g., angling the mandrel 40 anywhere up to 180° from the first dipping direction. This may be accomplished in one example through the use of one or more pivoting linkages 56, 58 connecting mandrel 40 to bracket arm 38, as illustrated. The one or more linkages 56, 58 may maintain mandrel 40 in a first vertical position relative to solution 46 to coat the initial layers of substrate 50, as shown in FIG. 2B. Linkages 56, 58 may then be actuated to reconfigure mandrel 40 from its first vertical position to a second vertical position opposite to the first vertical position, as indicated by direction 59 in FIG. 2C. With repositioning of mandrel 40 complete, the dipping process may be resumed by dipping the entire linkage assembly along with mandrel 40 and substrate 50. In this manner, neither mandrel 40 nor substrate 50 needs to be removed and thus eliminates any risk of contamination. Linkages 56, 58 may comprise any number of mechanical or electromechanical pivoting and/or rotating mechanisms as known in the art.

Dipping mandrel 40 and substrate 50 in different directions may also enable the coated layers to have a uniform thickness throughout from its proximal end to its distal end to help compensate for the effects of gravity during the coating process. These values are intended to be illustrative and are not intended to be limiting in any manner. Any excess dip-coated layers on the linkages 56, 58 may simply be removed from mandrel 40 by breaking the layers. Alternating the dipping direction may also result in the polymers being oriented alternately which may reinforce the tensile strength in the axial direction of the dip coated tubular substrate 50.

With dip-coating assembly 30, one or more high molecular weight biocompatible and/or bioabsorbable polymers may be selected for forming upon mandrel 40. Examples of polymers which may be utilized to form the polymeric substrate may include, but is not limited to, polyethylene, polycarbonates, polyamides, polyesteramides, polyetheretherketone, polyacetals, polyketals, polyurethane, polyolefin, or polyethylene terephthalate and degradable polymers, for example, polylactide (PLA) including poly-L-lactide (PLLA), poly-glycolide (PGA), poly(lactide-co-glycolide) (PLGA) or polycaprolactone, caprolactones, polydioxanones, polyanhydrides, polyorthocarbonates, polyphospliazenes, chitin, chitosan, poly (amino acids), and polyorthoesters, and copolymers, terpolymers and combinations and mixtures thereof.

Other examples of suitable polymers may include synthetic polymers, for example, oligomers, homopolymers, and co-polymers, acrylics such as those polymerized from methyl cerylate, methyl methacrylate, acrylic acid, methacrylic acid, acrylamide, hydroxyethy acrylate, hydroxyethyl methacrylate, glyceryl scrylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrfluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyactic acid, polyglycolic acid, polydimethylsiloxanes, and polyetherketones.

Examples of biodegradable polymers which can be used for dip-coating process are polylactide (PLA), polyglycolide (PGA), poly(lactide-co-glycolide) (PLGA), poly(e-caprolactone), polydioxanone, polyanhydride, trimethylene carbonate, poly($\beta$-hydroxybutyrate), poly(g-ethyl glutamate), poly (DTH iminocarbonate), poly(bisphenol A iminocarbonate), poly(ortho ester), polycyanoacrylate, and polyphosphazene, and copolymers, terpolymers and combinations and mixtures thereof. There are also a number of biodegradable polymers derived from natural sources such as modified polysaccharides (cellulose, chitin, chitosan, dextran) or modified proteins (fibrin, casein).

Other examples of suitable polymers may include synthetic polymers, for example, oligomers, homopolymers, and co-polymers, acrylics such as those polymerized from methyl cerylate, methyl methacrylate, acryli acid, methacrylic acid, acrylamide, hydroxyethy acrylate, hydroxyethyl methacrylate, glyceryl scrylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrfluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyacetals, polyketals, polydimethylsiloxanes, and polyetherketones.

These examples of polymers which may be utilized for forming the substrate are not intended to be limiting or exhaustive but are intended to be illustrative of potential polymers which may be used. As the substrate may be formed to have one or more layers overlaid upon one another, the substrate may be formed to have a first layer of a first polymer, a second layer of a second polymer, and so on depending upon the desired structure and properties of the substrate. Thus, the various solutions and containers may be replaced beneath mandrel 40 between dip-coating operations in accordance with the desired layers to be formed upon the substrate such that the mandrel 40 may be dipped sequentially into the appropriate polymeric solution.

Depending upon the desired wall thickness of the formed substrate, the mandrel 40 may be dipped into the appropriate solution as determined by the number of times the mandrel 40 is immersed, the duration of time of each immersion within the solution, as well as the delay time between each immersion or the drying or curing time between dips. Additionally, parameters such as the dipping and/or withdrawal rate of the mandrel 40 from the polymeric solution may also be controlled to range from, e.g., 5 mm/min to 1000 mm/min. Formation via the dip-coating process may result in a polymeric substrate having half the wall thickness while retaining an increased level of strength in the substrate as compared to an extruded polymeric structure. For example, to form a substrate having a wall thickness of, e.g., 200 µm, built up of multiple layers of polylactic acid, mandrel 40 may be dipped between, e.g., 2 to 20 times or more, into the polymeric solution with an immersion time ranging from, e.g., 15 seconds (or less) to 240 minutes (or more. Moreover, the substrate and mandrel 40 may be optionally dried or cured for a period of time ranging from, e.g., 15 seconds (or less) to 60 minutes (or more) between each immersion. These values are intended to be illustrative and are not intended to be limiting in any manner.

Aside from utilizing materials which are relatively high in molecular weight, another parameter which may be considered in further increasing the ductility of the material is its crystallinity, which refers to the degree of structural order in the polymer. Such polymers may contain a mixture of crystalline and amorphous regions where reducing the percentage of the crystalline regions in the polymer may further increase the ductility of the material. Polymeric materials not only having a relatively high molecular weight but also having a relatively low crystalline percentage may be utilized in the processes described herein to form a desirable tubular substrate.

The following Table 1 show examples of various polymeric materials (e.g., PLLA IV 8.28 and PDLLA 96/4) to illustrate the molecular weights of the materials in comparison to their respective crystallinity percentage. The glass transition temperature, $T_g$, as well as melting temperature, $T_m$, are given as well. An example of PLLA IV 8.28 is shown illustrating the raw resin and tube form as having the same molecular weight, $M_w$, of $1.70 \times 10^6$ gram/mol. However, the crystallinity percentage of PLLA IV 8.28 Resin is 61.90% while the corresponding Tube form is 38.40%. Similarly for PDLLA 96/4, the resin form and tube form each have a molecular weight, $M_w$, of $9.80 \times 10^5$ gram/mol; however, the crystallinity percentages are 46.20% and 20.90%, respectively.

TABLE 1

Various polymeric materials and their respective crystallinity percentages.

| Material | $T_g$ (° C.) | $T_m$ (° C.) | Crystallinity (%) | $M_w$ (gram/mol) |
|---|---|---|---|---|
| PLLA IV8.28 Resin | 72.5 | 186.4 | 61.90% | $1.70 \times 10^6$ |
| PLLA IV8.28 Tubes | 73.3 | 176.3 | 38.40% | $1.70 \times 10^6$ |
| PDLLA 96/4 Resin | 61.8 | 155.9 | 46.20% | $9.80 \times 10^5$ |
| PDLLA 96/4 Tubes | 60.3 | 146.9 | 20.90% | $9.80 \times 10^5$ |

As the resin is dip coated to form the tubular substrate through the methods described herein, the drying procedures and processing helps to preserve the relatively high molecular weight of the polymer from the starting material and throughout processing to substrate and stent formation. Moreover, the drying processes in particular may facilitate the formation of desirable crystallinity percentages, as described above.

Aside from the crystallinity of the materials, the immersion times as well as drying times may be uniform between each immersion or they may be varied as determined by the desired properties of the resulting substrate. Moreover, the substrate may be placed in an oven or dried at ambient temperature between each immersion or after the final immersion to attain a predetermined level of crystals, e.g., 60%, and a level of amorphous polymeric structure, e.g., 40%. Each of the layers overlaid upon one another during the dip-coating process are tightly adhered to one another and the mechanical properties of each polymer are retained in their respective layer with no limitation on the molecular weight of the polymers utilized.

Varying the drying conditions of the materials may also be controlled to effect desirable material parameters. The polymers may be dried at or above the glass transition temperature (e.g., 10° to 20° C. above the glass transition temperature, $T_g$) of the respective polymer to effectively remove any residual solvents from the polymers to attain residual levels of less than 100 ppm, e.g., between 20 to 100 ppm. Positioning of the polymer substrate when drying is another factor which may be controlled as affecting parameters, such as geometry, of the tube. For instance, the polymer substrate may be maintained in a drying position such that the substrate tube is held in a perpendicular position relative to the ground such that the concentricity of the tubes is maintained. The substrate tube may be dried in an oven at or above the glass transition temperature, as mentioned, for a period of time ranging anywhere from, e.g., 10 days to 30 days or more. However, prolonged drying for a period of time, e.g., greater than 40 days, may result in thermal degradation of the polymer material.

Additionally and/or optionally, a shape memory effect may be induced in the polymer during drying of the substrate. For instance, a shape memory effect may be induced in the polymeric tubing to set the tubular shape at the diameter that was formed during the dip-coating process. An example of this is to form a polymeric tube by a dip-coating process described herein at an outer diameter of 5 mm and subjecting the substrate to temperatures above its glass transition temperature, $T_g$. At its elevated temperature, the substrate may be elongated, e.g., from a length of 5 cm to 7 cm, while its outer diameter of 5 mm is reduced to 3 mm. Of course, these examples are merely illustrative and the initial diameter may generally range anywhere from, e.g., 3 mm to 9 mm, and the reduced diameter may generally range anywhere from, e.g., 1.5 mm to 5 mm, provided the reduced diameter is less than the initial diameter.

Once lengthened and reduced in diameter, the substrate may be quenched or cooled in temperature to a sub-$T_g$ level, e.g., about 20° C. below its $T_g$, to allow for the polymeric substrate to transition back to its glass state. This effectively imparts a shape memory effect of self-expansion to the original diameter of the substrate. When such a tube (or stent formed from the tubular substrate) is compressed or expanded to a smaller or larger diameter and later exposed to an elevated temperature, over time the tube (or stent) may revert to its original 5 mm diameter. This post processing may also be useful for enabling self-expansion of the substrate after a process like laser cutting (e.g., when forming stents or other devices for implantation within the patient) where the substrate tube is typically heated to its glass transition temperature, $T_g$.

Figure 3A:
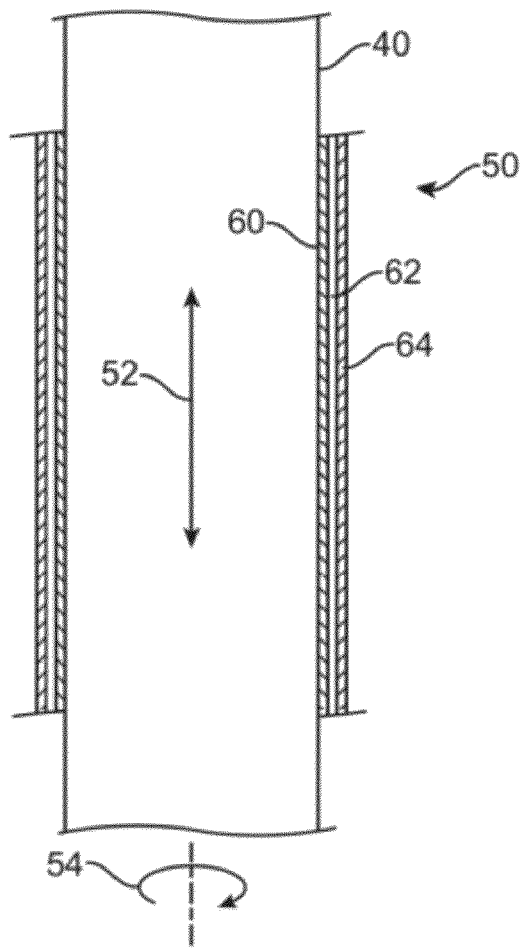
FIGS. 3A to 3C show respective partial cross-sectional side and end views of an example of a portion of a multi-layer polymeric substrate formed along the mandrel and the resulting substrate.
Figure 3B:
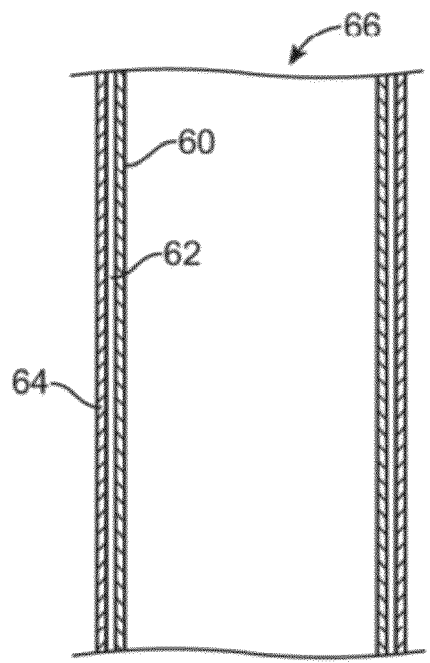

An example of a substrate having multiple layers is illustrated in FIGS. 3A and 3B which show partial cross-sectional side views of an example of a portion of a multi-layer polymeric substrate formed along mandrel 40 and the resulting substrate. Substrate 50 may be formed along mandrel 40 to have a first layer 60 formed of a first polymer, e.g., poly(l-lactide). After the formation of first layer 60, an optional second layer 62 of polymer, e.g., poly(L-lactide-co-glycolide), may be formed upon first layer 60. Yet another optional third layer 64 of polymer, e.g., poly(d,l-lactide-co-glycolide), may be formed upon second layer 62 to form a resulting substrate defining a lumen 66 therethrough which may be further processed to form any number of devices, such as a stent. One or more of the layers may be formed to degrade at a specified rate or to elute any number of drugs or agents.

Figure 3C:
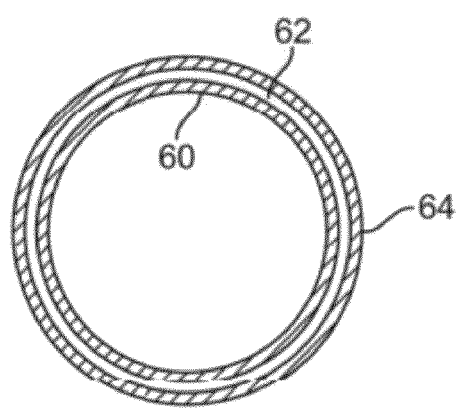

An example of this is illustrated in the cross-sectional end view of FIG. 3C, which shows an exemplary substrate having three layers 60, 62, 64 formed upon one another, as above. In this example, first layer 60 may have a molecular weight of $M_{n1}$, second layer 62 may have a molecular weight of $M_{n2}$, and third layer 64 may have a molecular weight of $M_{n3}$. A stent fabricated from the tube may be formed such that the relative molecular weights are such where $M_{n1} > M_{n2} > M_{n3}$ to achieve a preferential layer-by-layer degradation through the thickness of the tube beginning with the inner first layer 60 and eventually degrading to the middle second layer 62 and finally to the outer third layer 64 when deployed within the patient body. Alternatively, the stent may be fabricated where the relative molecular weights are such where $M_{n1} < M_{n2} < M_{n3}$ to achieve a layer-by-layer degradation beginning with the outer third layer 64 and degrading towards the inner first layer 60. This example is intended to be illustrative and fewer than or more than three layers may be utilized in other examples. Additionally, the molecular weights of each respective layer may be altered in other examples to vary the degradation rates along different layers, if so desired.

Moreover, any one or more of the layers may be formed to impart specified mechanical properties to the substrate 50 such that the composite mechanical properties of the resulting substrate 50 may specifically tuned or designed. Additionally, although three layers are illustrated in this example, any number of layers may be utilized depending upon the desired mechanical properties of the substrate 50.

Moreover, as multiple layers may be overlaid one another in forming the polymeric substrate, specified layers may be designated for a particular function in the substrate. For example, in substrates which are used to manufacture polymeric stents, one or more layers may be designed as load-bearing layers to provide structural integrity to the stent while certain other layers may be allocated for drug-loading or eluting. Those layers which are designated for structural support may be formed from high-molecular weight polymers, e.g., PLLA or any other suitable polymer described herein, to provide a high degree of strength by omitting any drugs as certain pharmaceutical agents may adversely affect the mechanical properties of polymers. Those layers which are designated for drug-loading may be placed within, upon, or between the structural layers.

Additionally, multiple layers of different drugs may be loaded within the various layers. The manner and rate of drug release from multiple layers may depend in part upon the degradation rates of the substrate materials. For instance, polymers which degrade relatively quickly may release their drugs layer-by-layer as each successive layer degrades to expose the next underlying layer. In other variations, drug release may typically occur from a multilayer matrix via a combination of diffusion and degradation. In one example, a first layer may elute a first drug for, e.g., the first 30 to 40 days after implantation. Once the first layer has been exhausted or degraded, a second underlying layer having a second drug may release this drug for the next 30 to 40 days, and so on if so desired. In the example of FIG. 3B, for a stent (or other implantable device) manufactured from substrate 50, layer 64 may contain the first drug for release while layer 62 may contain the second drug for release after exhaustion or degradation of layer 64. The underlying layer 60 may omit any pharmaceutical agents to provide uncompromised structural support to the entire structure.

In other examples, rather than having each successive layer elute its respective drug, each layer 62, 64 (optionally layer 60 as well), may elute its respective drug simultaneously or at differing rates via a combination of diffusion and degradation. Although three layers are illustrated in this example, any number of layers may be utilized with any practicable combination of drugs for delivery. Moreover, the release kinetics of each drug from each layer may be altered in a variety of ways by changing the formulation of the drug-containing layer.

Examples of drugs or agents which may be loaded within certain layers of substrate 50 may include one or more anti-poliferative, antineoplastic, antigenic, anti-inflammatory, and/or antirestenotic agents. The therapeutic agents may also include antilipid, antimitotics, metalloproteinase inhabitors, anti-sclerosing agents. Therapeutic agents may also include peptides, enzymes, radio isotopes or agents for a variety of treatment options. This list of drugs or agents is presented to be illustrative and is not intended to be limiting.

Similarly certain other layers may be loaded with radio-opaque substances such as platinum, gold, etc. to enable visibility of the stent under imaging modalities such as fluoroscopic imaging. Radio-opaque substances like tungsten, platinum, gold, etc. can be mixed with the polymeric solution and dip-coated upon the substrate such that the radio-opaque substances form a thin sub-micron thick layer upon the substrate. The radio-opaque substances may thus become embedded within layers that degrade in the final stages of degradation or within the structural layers to facilitate stent visibility under an imaging modality, such as fluoroscopy, throughout the life of the implanted device before fully degrading or losing its mechanical strength. Radio-opaque marker layers can also be dip-coated at one or both ends of substrate 50, e.g., up to 0.5 mm from each respective end. Additionally, the radio-opaque substances can also be spray-coated or cast along a portion of the substrate 50 between its proximal and distal ends in a radial direction by rotating mandrel 40 when any form of radio-opaque substance is to be formed along any section of length of substrate 50. Rings of polymers having radio-opaque markers can also be formed as part of the structure of the substrate 50.

Figure 4A:
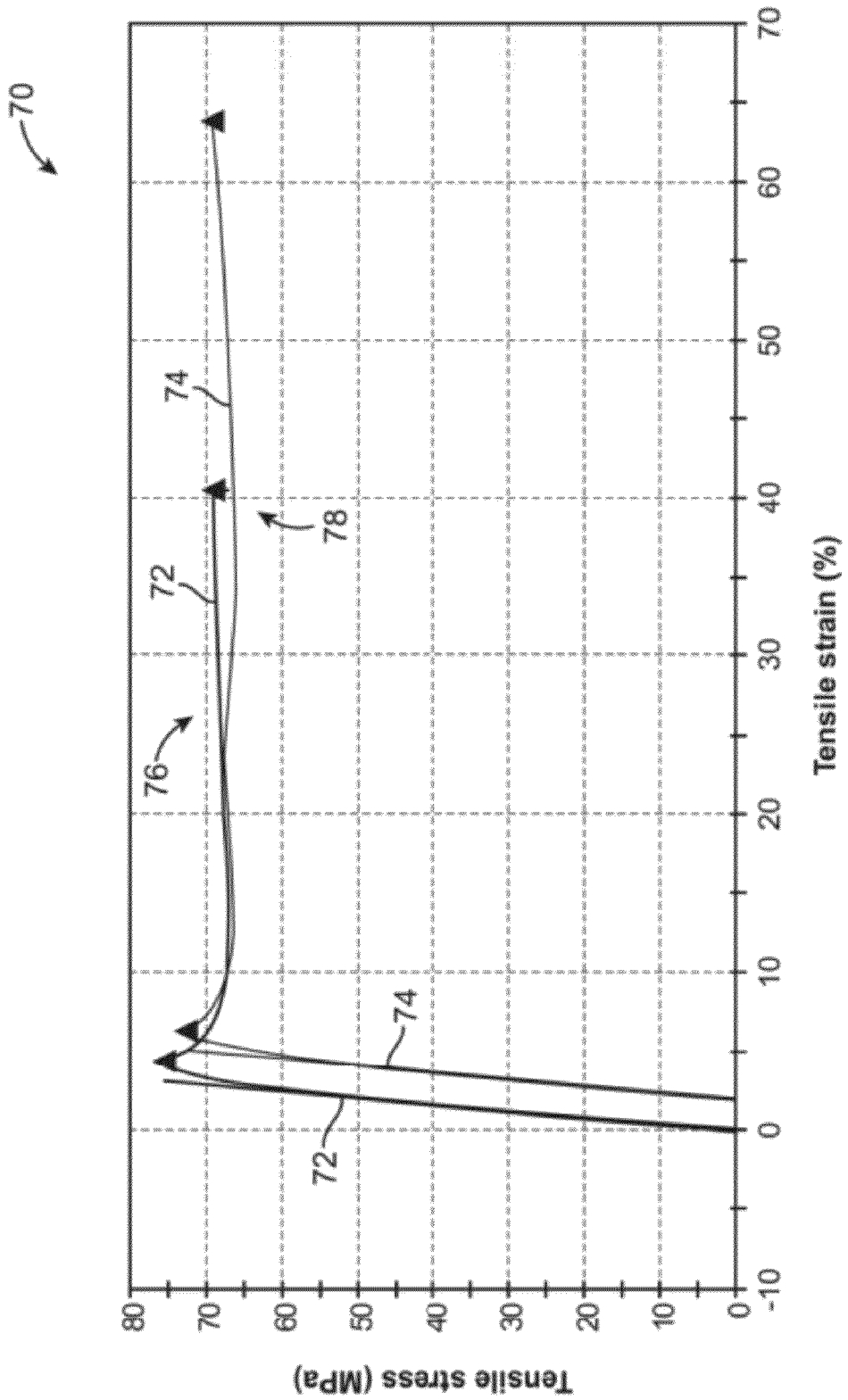
FIG. 4A illustrates an example of a resulting stress-strain plot of various samples of polymeric substrates formed by a dip-coating process and the resulting plots indicating ductile failure.

In an experimental example of the ductility and retention of mechanical properties, PLLA with Iv 8.4 (high molecular weight) was obtained and tubular substrates were manufactured utilizing the dip-coating process described herein. The samples were formed to have a diameter of 5 mm with a wall thickness of 200 µm and were comprised of 6 layers of PLLA 8.4. The mandrel was immersed 6 times into the polymeric solution and the substrates were dried or cured in an oven to obtain a 60% crystalline structure. At least two samples of tubular substrates were subjected to tensile testing and stress-strain plot 70 was generated from the stress-strain testing, as shown in FIG. 4A.

As shown in plot 70, a first sample of PLLA 8.4 generated a stress-strain curve 72 having a region of plastic failure 76 where the strain percentage increased at a relatively constant stress value prior to failure indicating a good degree of sample ductility. A second sample of PLLA 8.4 also generated a stress-strain curve 74 having a relatively greater region of plastic failure 78 also indicating a good degree of sample ductility.

Polymeric stents and other implantable devices made from such substrates may accordingly retain the material properties from the dip-coated polymer materials. The resulting stents, for instance, may exhibit mechanical properties which have a relatively high percentage ductility in radial, torsional, and/or axial directions. An example of this is a resulting stent having an ability to undergo a diameter reduction of anywhere between 5% to 70% when placed under an external load without any resulting plastic deformation. Such a stent may also exhibit high radial strength with, e.g., a 20% radial deformation when placed under a 0.1 N to 20 N load. Such a stent may also be configured to self-expand when exposed to normal body temperatures.

The stent may also exhibit other characteristic mechanical properties which are consistent with a substrate formed as described herein, for instance, high ductility and high strength polymeric substrates. Such substrates (and processed stents) may exhibit additional characteristics such as a percent reduction in diameter of between 5% to 70% without fracture formation when placed under a compressive load as well as a percent reduction in axial length of between 10% to 30% without fracture formation when placed under an axial load. Because of the relatively high ductility, the substrate or stent may also be adapted to curve up to 180° about a 1 cm curvature radius without fracture formation or failure. Additionally, when deployed within a vessel, a stent may also be expanded, e.g., by an inflatable intravascular balloon, by up to 5% to 70% to regain diameter without fracture formation or failure.

These values are intended to illustrate examples of how a polymeric tubing substrate and a resulting stent may be configured to yield a device with certain mechanical properties. Moreover, depending upon the desired results, certain tubes and stents may be tailored for specific requirements of various anatomical locations within a patient body by altering the polymer and/or copolymer blends to adjust various properties such as strength, ductility, degradation rates, etc.

Figure 4B:
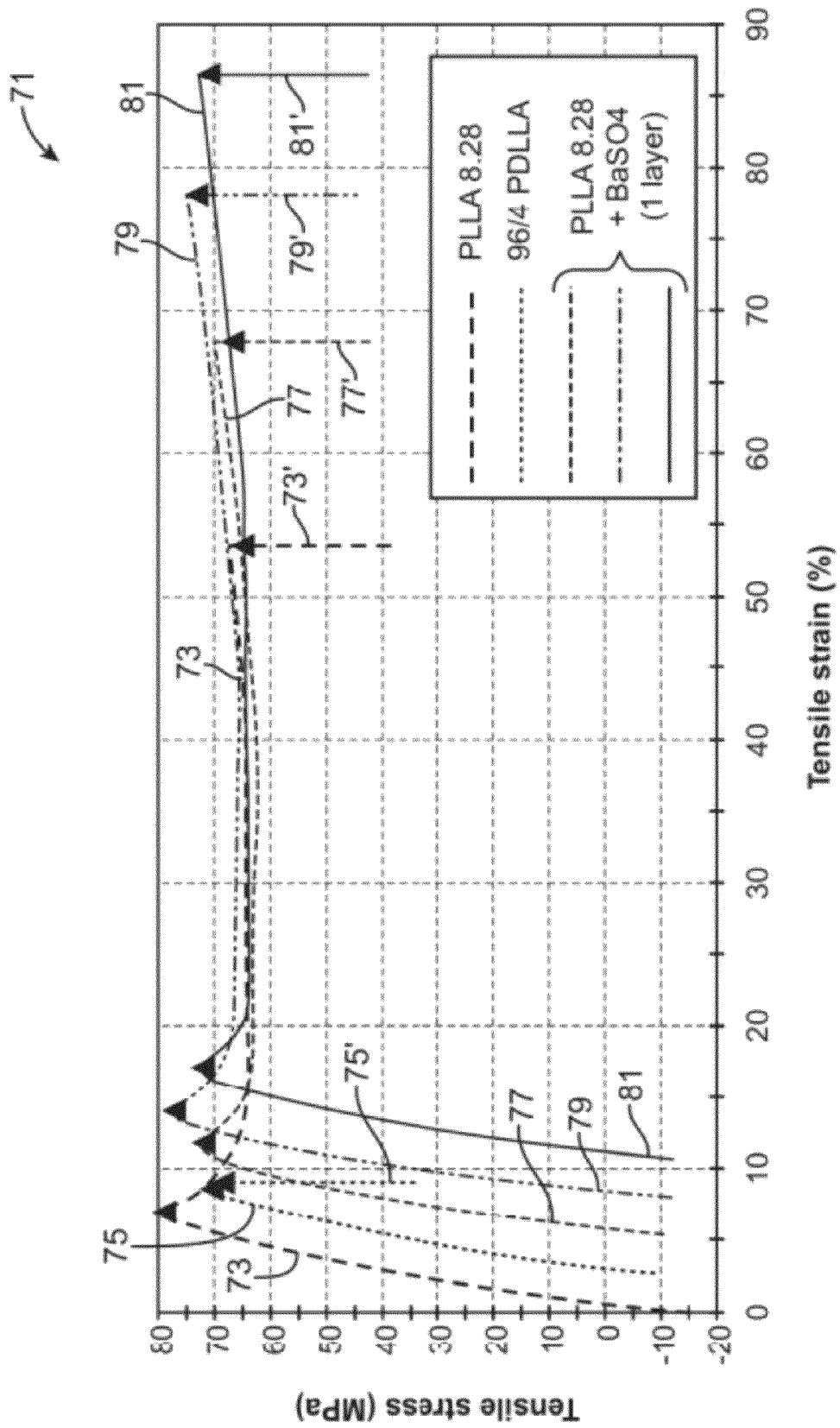
FIG. 4B illustrates another example of a stress-strain plot of additional samples formed by dip-coating along with samples incorporating a layer of $BaSO_4$.

FIG. 4B illustrates a plot 71 of additional results from stress-strain testing with additional polymers. A sample of PLLA 8.28 was formed utilizing the methods described herein and tested to generate stress-strain curve 73 having a point of failure 73'. Additional samples of PLLA 8.28 each with an additional layer of $BaSO_4$ incorporated into the tubular substrate were also formed and tested. A first sample of PLLA 8.28 with a layer of $BaSO_4$ generated stress-strain curve 77 having a point of failure 77'. A second sample of PLLA 8.28 also with a layer of $BaSO_4$ generated stress-strain curve 79 having a point of failure 79', which showed a greater tensile strain than the first sample with a slightly higher tensile stress level. A third sample of PLLA 8.28 with a layer of $BaSO_4$ generated stress-strain curve 81 having a point of failure 81', which was again greater than the tensile strain of the second sample, yet not significantly greater than the tensile stress level. The inclusion of $BaSO_4$ may accordingly improve the elastic modulus values of the polymeric substrates. The samples of PLLA 8.28 generally resulted in a load of between 100 N to 300 N at failure of the materials, which yielded elastic modulus values of between 1000 to 3000 MPa with a percent elongation of between 10% to 300% at failure.

A sample of 96/4 PDLLA was also formed and tested to generate stress-strain curve 75 having a point of failure 75' which exhibited a relatively lower percent elongation characteristic of brittle fracture. The resulting load at failure was between 100 N to 300 N with an elastic modulus of between 1000 to 3000 MPa, which was similar to the PLLA 8.28 samples. However, the percent elongation was between 10% to 40% at failure.

Figure 4C:
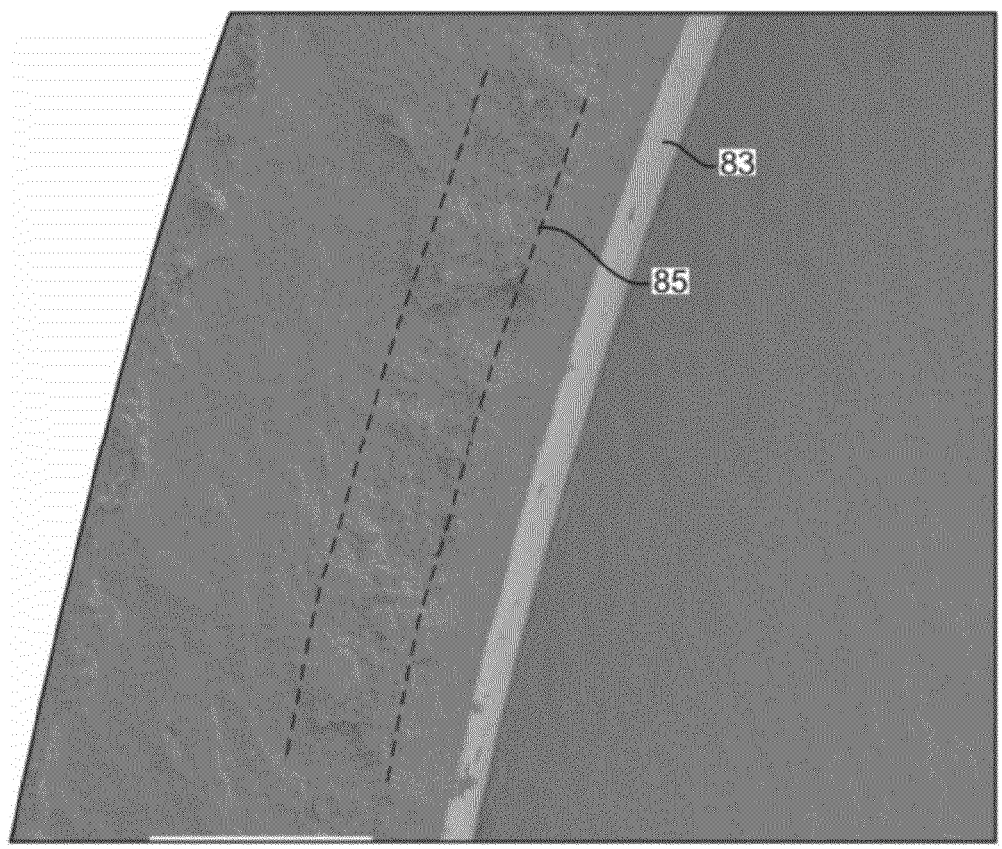
FIG. 4C illustrates an example of a detailed end view of a PLLA 8.28 substrate having a $BaSO_4$ layer incorporated into the substrate.

FIG. 4C illustrates an example of a detailed end view of a PLLA 8.28 substrate 83 formed with multiple dip-coated layers via a process described herein as viewed under a scanning electron microscope. This variation has a $BaSO_4$ layer 85 incorporated into the substrate. As described above, one or more layers of $BaSO_4$ may be optionally incorporated into substrate 83 to alter the elastic modulus of the formed substrate. Additionally, the individual layers overlaid atop one another are fused to form a single cohesive layer rather than multiple separate layers as a result of the drying processes during the dipping process described herein. This results in a unitary structure which further prevents or inhibits any delamination from occurring between the individual layers.

Figure 5A:
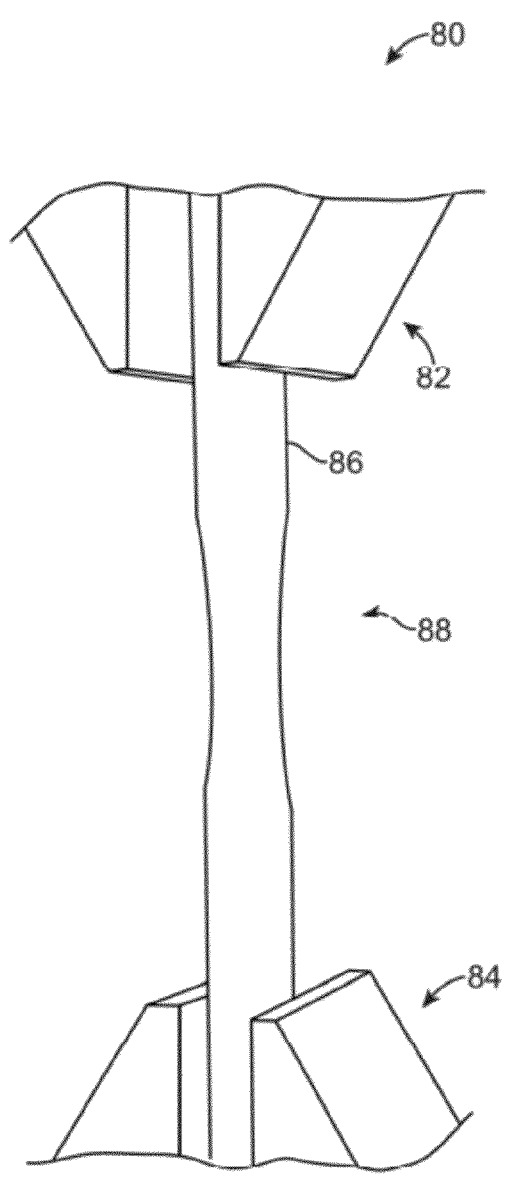
FIGS. 5A and 5B illustrate perspective views of an example of a dip-coat formed polymeric substrate undergoing plastic deformation and the resulting high percentage elongation.
Figure 5B:
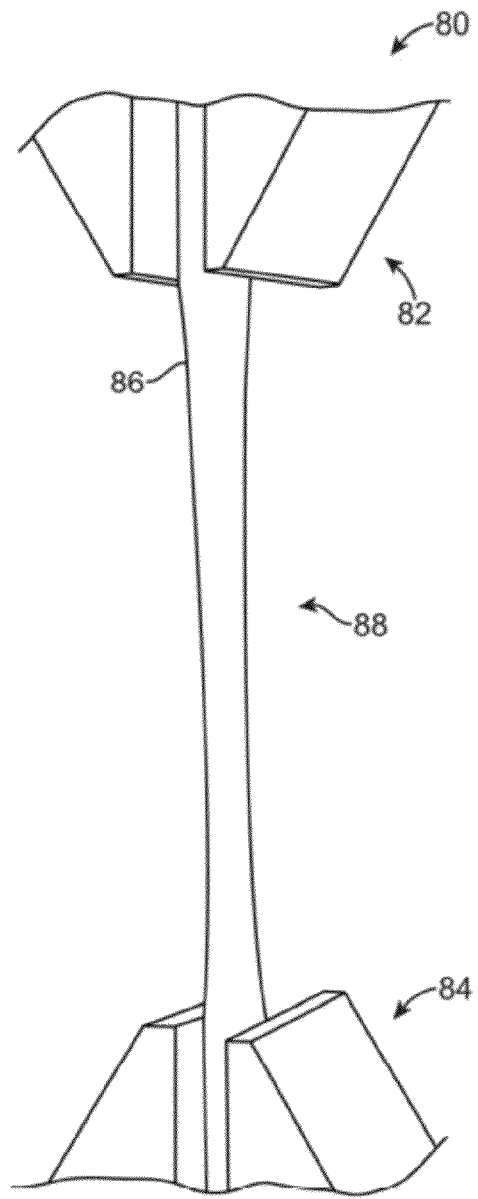

FIGS. 5A and 5B illustrate perspective views of one of the samples which was subjected to stress-strain testing on tensile testing system 80. The polymeric substrate specimen 86 was formed upon a mandrel, as described above, into a tubular configuration and secured to testing platform 82, 84. With testing platform 82, 84 applying tensile loading, substrate specimen 86 was pulled until failure. The relatively high percentage of elongation is illustrated by the stretched region of elongation 88 indicating a relatively high degree of plastic deformation when compared to an extruded polymeric substrate. Because a polymeric substrate formed via dip-coating as described above may be reduced in diameter via plastic deformation without failure, several different stent diameters can be manufactured from a single diameter substrate tube.

Dip-coating can be used to impart an orientation between layers (e.g., linear orientation by dipping; radial orientation by spinning the mandrel; etc.) to further enhance the mechanical properties of the formed substrate. As radial strength is a desirable attribute of stent design, post-processing of the formed substrate may be accomplished to impart such attributes. Typically, polymeric stents suffer from having relatively thick walls to compensate for the lack of radial strength, and this in turn reduces flexibility, impedes navigation, and reduces arterial luminal area immediately post implantation. Post-processing may also help to prevent material creep and recoil (creep is a time-dependent permanent deformation that occurs to a specimen under stress, typically under elevated temperatures) which are problems typically associated with polymeric stents.

In further increasing the radial or circumferential strength of the polymeric substrate, a number of additional processes may be applied to the substrate after the dip-coating procedure is completed (or close to being completed). A polymer that is amorphous or that is partially amorphous will generally undergo a transition from a pliable, elastic state (at higher temperatures) to a brittle glass-like state (at lower temperature) as it transitions through a particular temperature, referred as the glass transition temperature ($T_g$). The glass transition temperature for a given polymer will vary, depending on the size and flexibility of side chains, as well as the flexibility of the backbone linkages and the size of functional groups incorporated into the polymer backbone. Below $T_g$, the polymer will maintain some flexibility, and may be deformed to a new shape. However, the further the temperature below $T_g$ the polymer is when being deformed, the greater the force needed to shape it.

Moreover, when a polymer is in glass transition temperature its molecular structure can be manipulated to form an orientation in a desired direction. Induced alignment of polymeric chains or orientation improves mechanical properties and behavior of the material. Molecular orientation is typically imparted by application of force while the polymer is in a pliable, elastic state. After sufficient orientation is induced, temperature of the polymer is reduced to prevent reversal and dissipation of the orientation.

In one example, the polymeric substrate may be heated to increase its temperature along its entire length or along a selected portion of the substrate to a temperature that is at or above the $T_g$ of the polymer. For instance, for a substrate fabricated from PLLA, the substrate may be heated to a temperature between 60° C. to 70° C. Once the substrate has reached a sufficient temperature such that enough of its molecules have been mobilized, a force may be applied from within the substrate or along a portion of the substrate to increase its diameter from a first diameter $D_1$ to a second increased diameter $D_2$ for a period of time necessary to set the increased diameter. During this setting period, the application of force induces a molecular orientation in a circumferential direction to align the molecular orientation of polymer chains to enhance its mechanical properties. The re-formed substrate may then be cooled to a lower temperature typically below $T_g$, for example, by passing the tube through a cold environment, typically dry air or an inert gas to maintain the shape at diameter $D_2$ and prevent dissipation of molecular orientation.

The force applied to the substrate may be generated by a number of different methods. One method is by utilizing an expandable pressure vessel placed within the substrate. Another method is by utilizing a braid structure, such as a braid made from a super-elastic or shape memory alloy like NiTi alloy, to increase in size and to apply the desirable degree of force against the interior surface of the substrate.

Figure 6:
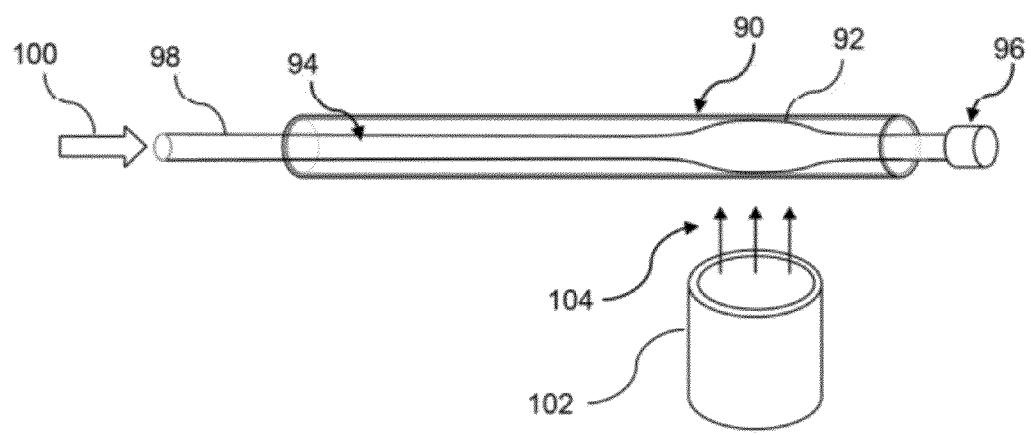
FIG. 6 illustrates an example of an additional forming procedure where a formed polymeric substrate may be expanded within a molding or forming tube to impart a circumferential orientation into the substrate.

Yet another method may apply the expansion force by application of a pressurized inert gas such as nitrogen within the substrate lumen, as shown in FIG. 6, to impart a circumferential orientation in the substrate. A completed substrate, e.g., cast cylinder 94, may be placed inside a molding tube 90 which has an inner diameter that is larger than the cast cylinder 94. Molding tube 90 may be fabricated from glass, highly-polished metal, or polymer. Moreover, molding tube 90 may be fabricated with tight tolerances to allow for precision sizing of cast cylinder 94.

A distal end or distal portion of cast cylinder 94 may be clamped 96 or otherwise closed and a pressure source may be coupled to a proximal end 98 of cast cylinder 94. The entire assembly may be positioned over a nozzle 102 which applies heat 104 to either the length of cast cylinder 94 or to a portion of cast cylinder 94. The pressurized inert gas 100, e.g., pressured to 10 to 400 psi, may be introduced within cast cylinder 94 to increase its diameter, e.g., 2 mm, to that of the inner diameter, e.g., 4 mm, of molding tube 90. The increase in diameter of cast cylinder 94 may thus realign the molecular orientation of cast cylinder 94 to increase its radial strength and to impart a circumferential orientation in the cast cylinder 94. Portion 92 illustrates radial expansion of the cast cylinder 94 against the inner surface of the molding tube 90 in an exaggerated manner to illustrate the radial expansion and impartation of circumferential strength. After the diameter has been increased, cast cylinder 94 may be cooled, as described above.

Once the substrate has been formed and reduced in diameter to its smaller second diameter, the stent may be processed, as described above. Alternatively, the stent may be processed from the substrate after initial formation. The stent itself may then be reduced in diameter to its second reduced diameter.

In either case, once the stent has been formed into its second reduced diameter, the stent may be delivered to a targeted location within a vessel of a patient. Delivery may be effected intravascularly utilizing known techniques with the stent in its second reduced delivery diameter positioned upon, e.g., an inflation balloon, for intravascular delivery. Once the inflation catheter and stent has been positioned adjacent to the targeted region of vessel, the stent may be initially expanded into contact against the interior surface of the vessel.

With the stent expanded into contact against the vessel wall at a third diameter which is larger than the second delivery diameter, the inflation balloon may be removed from the stent. Over a predetermined period of time and given the structural characteristics of the stent, the stent may then also self-expand further into contact against the vessel wall for secure placement and positioning.

Because thermoplastic polymers such as PLLA typically soften when heated, the cast cylinder 94 or a portion of the cast cylinder 94 may be heated in an inert environment, e.g., a nitrogen gas environment, to minimize its degradation.

Figure 7:
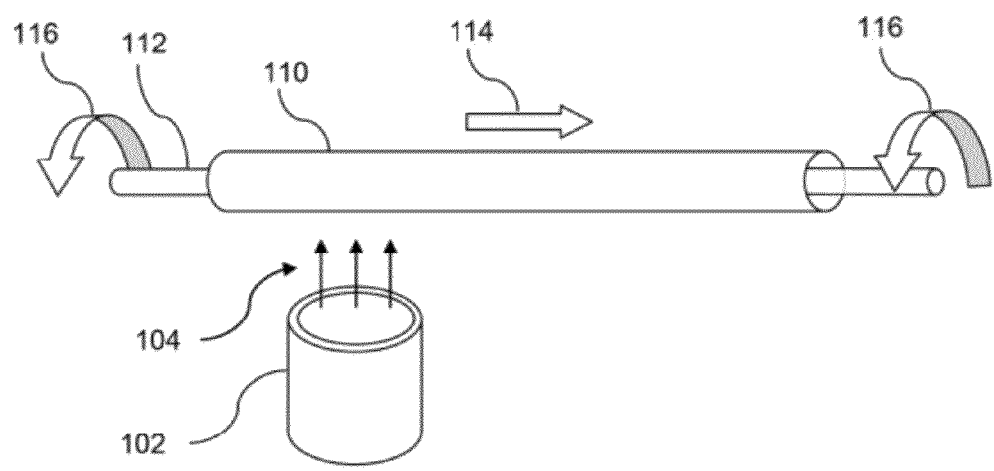
FIG. 7 illustrates another example of an additional forming procedure where a formed polymeric substrate may be rotated to induce a circumferentially-oriented stress value to increase the radial strength of the substrate.

Another method for post-processing a cast cylinder 110 may be seen in the example of FIG. 7 for inducing a circumferential orientation in the formed substrate. As illustrated, mandrel 112 having the cast cylinder 110 may be re-oriented into a horizontal position immediately post dip-coating before the polymer is cured. Mandrel 112 may be rotated, as indicated by rotational movement 116, at a predetermined speed, e.g., 1 to 300 rpm, while the cylinder 110 is heated via nozzle 102. Mandrel 112 may also be optionally rotated via motor 48 of assembly 30 to impart the rotational motion 54, as shown above in FIG. 2. Mandrel 112 may also be moved in a linear direction 114 to heat the length or a portion of the length of the cylinder 110. As above, this post-processing may be completed in an inert environment.

Figure 8:
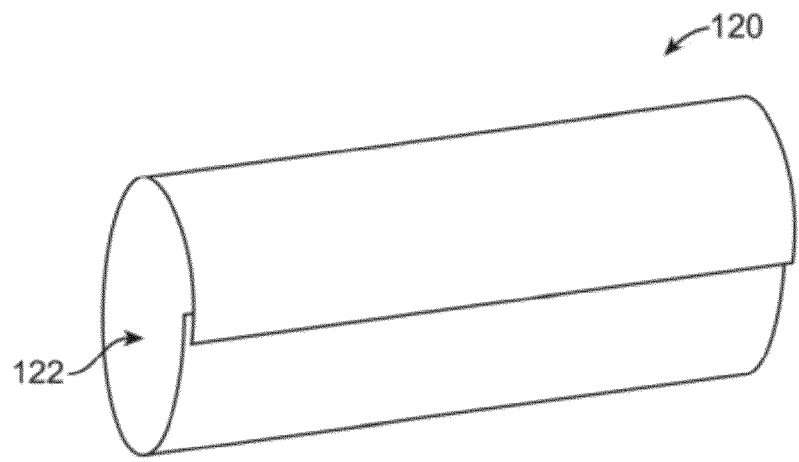
FIG. 8 illustrates a perspective view of one example of a rolled sheet stent which may be formed with the formed polymeric substrate.
Figure 9:
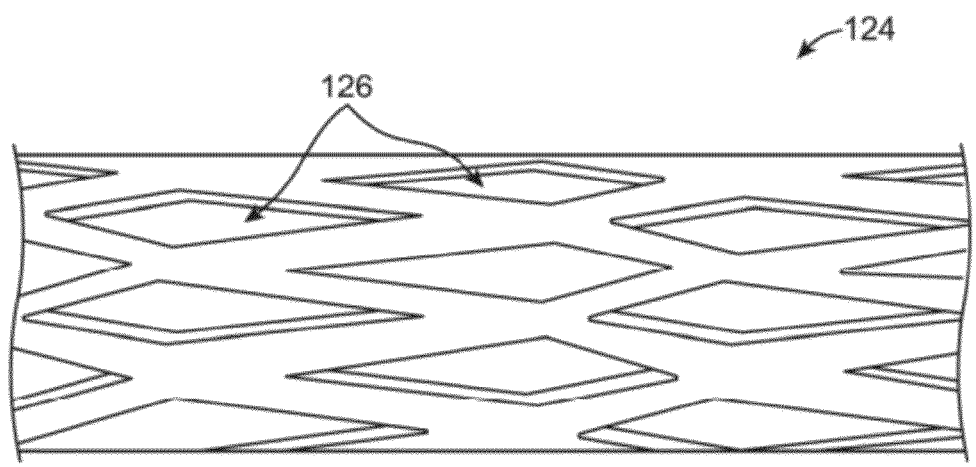
FIG. 9 illustrates a side view of another example of a stent machined via any number of processes from the resulting polymeric substrate.

Once the processing has been completed on the polymeric substrate, the substrate may be further formed or machined to create a variety of device. One example is shown in the perspective view of FIG. 8, which illustrates rolled stent 120. Stent 120 may be created from the cast cylinder by cutting along a length of the cylinder to create an overlapping portion 122. The stent 120 may then be rolled into a small configuration for deployment and then expanded within the patient vasculature. Another example is illustrated in the side view of stent 124, which may be formed by machining a number of removed portions 126 to create a lattice or scaffold structure which facilitates the compression and expansion of stent 124 for delivery and deployment.

Figure 10A:
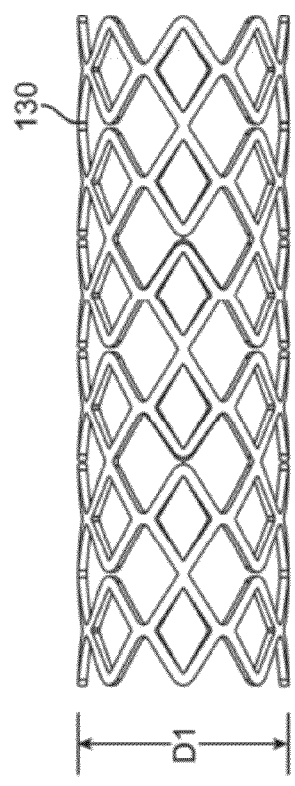
FIGS. 10A to 10F illustrate side views of another example of how a stent formed from a polymeric substrate may be delivered and deployed initially via balloon expansion within a vessel and then allowed to self-expand further in diameter to its initial heat set diameter.
Figure 10B:
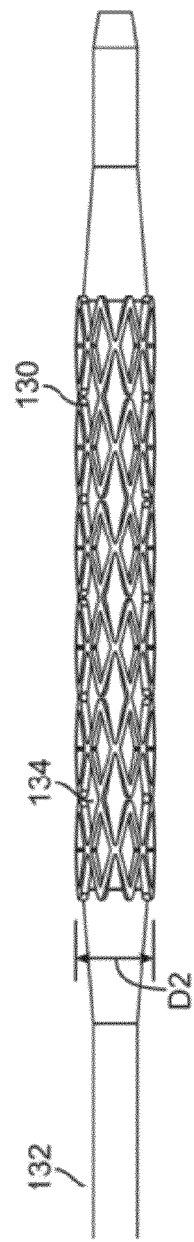

FIGS. 10A to 10F illustrate side views of another example of how a stent 130 formed from a polymeric substrate may be delivered and deployed for secure expansion within a vessel. FIG. 10A shows a side view of an exemplary stent 130 which has been processed or cut from a polymeric substrate formed with an initial diameter D1. As described above, the substrate may be heat treated at, near, or above the glass transition temperature $T_g$ of the substrate to set this initial diameter D1 and the substrate may then be processed to produce the stent 130 such that the stent 130 has a corresponding diameter D1. Stent 130 may then be reduced in diameter to a second delivery diameter D2 which is less than the initial diameter D1 such that the stent 130 may be positioned upon, e.g., an inflation balloon 134 of a delivery catheter 132, as shown in FIG. 10B. The stent 130 at its reduced diameter D2 may be self-constrained such that the stent 130 remains in its reduced diameter D2 without the need for an outer sheath, although a sheath may be optionally utilized. Additionally, because of the processing and the resultant material characteristics of the stent material, as described above, the stent 130 may be reduced from initial diameter D1 to delivery diameter D2 without cracking or material failure.

Figure 10C:
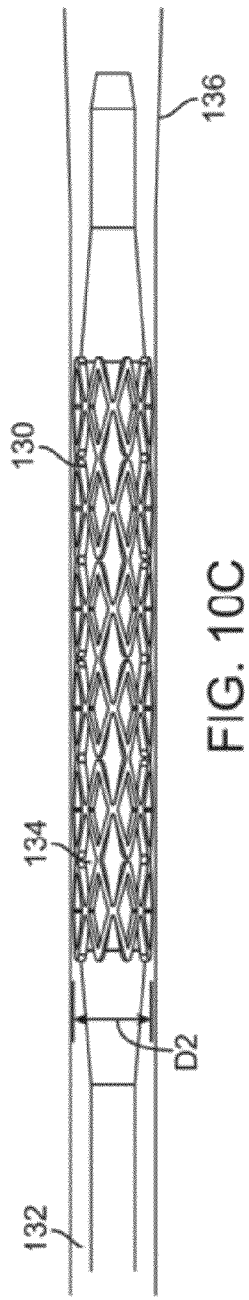
Figure 10D:
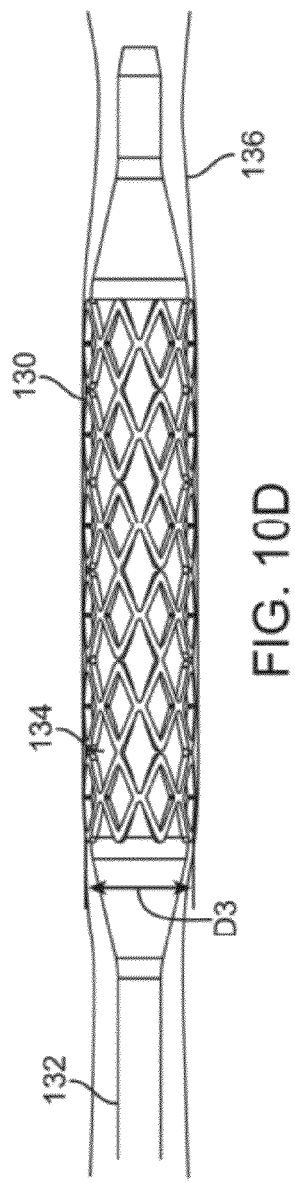
Figure 10E:
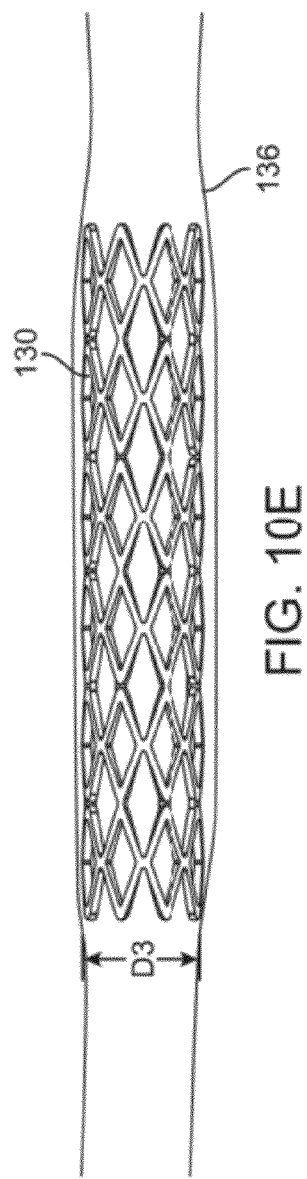

With stent 130 positioned upon delivery catheter 132, it may be advanced intravascularly within a vessel 136 until the delivery site is reached, as shown in FIG. 10C. Inflation balloon 134 may be inflated to expand a diameter of stent 130 into contact against the vessel interior, e.g., to an intermediate diameter D3, which is less than the stent's initial diameter D1 yet larger than the delivery diameter D2. Stent 130 may be expanded to this intermediate diameter D3 without any cracking or failure because of the inherent material characteristics described above. Moreover, expansion to intermediate diameter D3 may allow for the stent 130 to securely contact the vessel wall while allowing for the withdrawal of the delivery catheter 132, as shown in FIG. 10E.

Figure 10F:
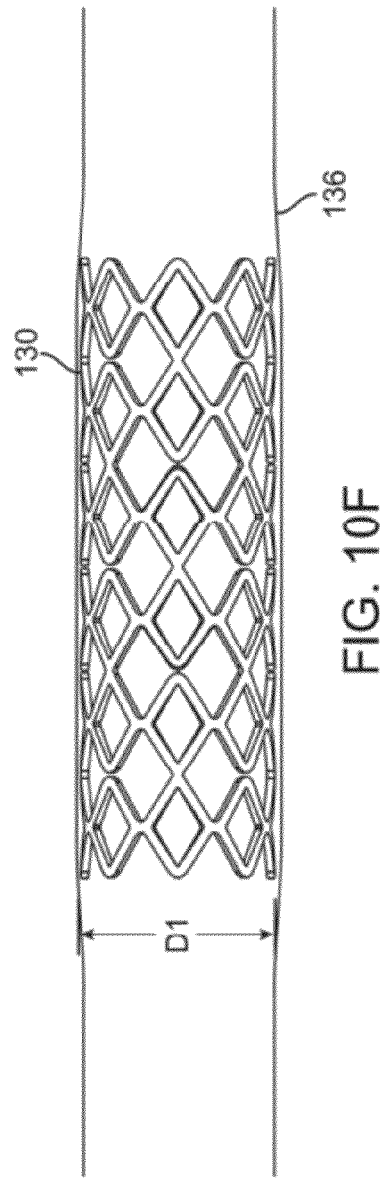

Once the stent 130 has been expanded to some intermediate diameter D3 and secured against the vessel wall, stent 130 may be allowed to then self-expand further over a period of time into further contact with the vessel wall such that stent 130 conforms securely to the tissue. This self-expansion feature ultimately allows for the stent 130 to expand back to its initial diameter D1 which had been heat set, as shown in FIG. 10F, or until stent 130 has fully self-expanded within the confines of the vessel diameter.

These examples are presented to be illustrative of the types of devices which may be formed and various other devices which may be formed from the polymeric substrate are also included within this disclosure.

The applications of the disclosed invention discussed above are not limited to certain processes, treatments, or placement in certain regions of the body, but may include any number of other processes, treatments, and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of dip-coating a polymeric substrate, comprising:
   immersing a mandrel into at least a first polymeric solution having an inherent viscosity of about 4.3 to about 8.4 dl/g such that at least a first layer of a biocompatible polymer substrate is formed upon the mandrel and has a first diameter defined by the mandrel;
   curing the substrate;
   subjecting the substrate to a first elevated temperature at or above a glass transition temperature of the substrate;
   cooling the substrate in a controlled manner to a second temperature lower than the glass transition temperature such that the substrate transitions to a glass state and imparts a shape memory effect;
   forming an expandable stent scaffold having the first diameter from the substrate; and
   reducing the first diameter of the stent to a second smaller diameter, wherein the stent retains one or more mechanical properties of the polymer resin such that the stent exhibits ductility upon application of a load.

2. The method of claim 1 wherein prior to forming an expandable stent scaffold, further comprising:
   controlling a number of immersions of the mandrel into the first polymeric solution;
   controlling a duration of time of each immersion of the mandrel; and
   controlling a delay time between each immersion of the mandrel.

3. The method of claim 2 further comprising controlling a withdrawal rate of the mandrel from the first polymeric solution after each immersion.

4. The method of claim 1 wherein the first polymeric solution comprises a polymer having a relatively high molecular weight.

5. The method of claim 1 wherein the first polymeric solution is selected from the group consisting of polyethylene, polycarbonates, polyamides, polyesteramides, polyetheretherketone, polyacetals, polyketals, polyurethane, polyolefin, polyethylene terephthalate, polylactide, poly-L-lactide, polyglycolide, poly(lactide-co-glycolide), polycaprolactone, caprolactones, polydioxanones, polyanhydrides, polyorthocarbonates, polyphosphazenes, chitin, chitosan, poly(amino acids), polyorthoesters, oligomers, homopolymers, methyl cerylate, methyl methacrylate, acryli acid, methacrylic acid, acrylamide, hydroxyethy acrylate, hydroxyethyl methacrylate, glyceryl scrylate, glyceryl methacrylate, methacrylamide, ethacrylamide, styrene, vinyl chloride, binaly pyrrolidone, polyvinyl alcohol, polycoprolactam, polylauryl lactam, polyjexamethylene adipamide, polyexamethylene dodecanediamide, trimethylene carbonate, poly($\beta$-hydroxybutyrate), poly(g-ethyl glutamate), poly(DTH iminocarbonate), poly(bisphenol A iminocarbonate), polycyanoacrylate, polyphosphazene, methyl cerylate, methyl methacrylate, acryli acid, methacrylic acid, acrylamide, hydroxyethy acrylate, hydroxyethyl methacrylate, glyceryl scrylate, glyceryl methacrylate, methacrylamide, ethacrylamide, and copolymers, terpolymers and combinations and mixtures thereof.

6. The method of claim 1 wherein immersing a mandrel comprises further immersing the mandrel into a second polymeric solution such that a second layer of polymer is formed upon the first layer.

7. The method of claim 6 wherein the second polymeric solution comprises a drug or agent selected from the group consisting of antipoliferative, antineoplastic, antigenic, anti-inflammatory, antirestenotic, antilipid, antimitotics, metallo-proteinase inhibitors, and anti-sclerosing agents.

8. The method of claim 6 wherein the second polymeric solution comprises a radio-opaque material.

9. The method of claim 8 wherein the mandrel is immersed at one or both ends of the substrate into the radio-opaque material.

10. The method of claim 6 wherein the second polymeric solution comprises a $BaSO_4$ solution.

11. The method of claim 2 wherein controlling a number of immersions comprises immersing the mandrel between 2 and 20 times.

12. The method of claim 2 wherein controlling a duration of time comprises immersing the mandrel between 15 seconds and 240 minutes.

13. The method of claim 2 wherein controlling a delay time comprises delaying immersion of the mandrel between 15 seconds and 60 minutes.

14. The method of claim 1 wherein immersing a mandrel comprises inserting the mandrel into the first polymeric solution at a rate of 5 mm/min to 1000 mm/min.

15. The method of claim 1 further comprising applying a force within a lumen defined through the polymeric substrate such that the substrate expands from a first diameter to a second larger diameter.

16. The method of claim 15 wherein applying a force comprises introducing a pressurized gas within the lumen.

17. The method of claim 15 further comprising constraining expansion of the polymeric substrate via a molding tube.

18. The method of claim 17 further comprising expanding at least a portion of the polymeric substrate into a shape defined by the molding tube.

19. The method of claim 15 further comprising applying heat to the polymeric substrate while applying the force.

20. The method of claim 1 further comprising rotating the mandrel while applying heat.

21. The method of claim 1 further comprising controlling an angle of the mandrel relative to the polymeric solution.

22. The method of claim 21 wherein controlling an angle comprises alternating an angle of the mandrel up to 180°.

23. The method of claim 1 wherein the substrate has a length of 1 cm to 40 cm.

24. The method of claim 1 further comprising controlling a relative humidity of less than 30%.

25. The method of claim 1 further comprising controlling a temperature of the polymeric solution to be below a boiling point of a solvent contained within the polymeric solution.

26. The method of claim 1 further comprising mold-transferring one or more patterns from an outer surface of the mandrel to an inner surface of the substrate.

27. The method of claim 1 further comprising controlling a crystallinity percentage of the substrate.

28. The method of claim 1 wherein the substrate formed upon the mandrel is isotropic.

29. The method of claim 1 curing the substrate comprises drying the substrate at a glass transition temperature of the polymeric solution.

30. The method of claim 1 wherein subjecting the substrate to a first elevated temperature comprises subjecting the substrate to the first elevated temperature above the glass transition temperature of the substrate while reducing the first diameter.

31. The method of claim 30 wherein reducing comprises reducing the first diameter ranging from 3 mm to 9 mm to the second diameter ranging from 1.5 mm to 5 mm.

32. The method of claim 30 wherein cooling comprises reducing the substrate temperature to the second temperature below the glass transition temperature.

33. The method of claim 1 wherein the expandable stent scaffold exhibits a 20% radial deformation when placed under a 0.1 N to 20 N load.

34. The method of claim 1 wherein the expandable stent scaffold exhibits a percent reduction in diameter of between 5% to 70% without fracture formation when placed under a compressive load.

35. The method of claim 1 wherein forming an expandable stent scaffold comprises machining the stent from the substrate.

36. The method of claim 35 further comprising expanding a diameter of the stent via an expandable balloon by 5% to 70% without fracture formation.

37. The method of claim 35 wherein the stent is adapted to curve up to 180° about a 1 cm curvature radius without fracture formation.

38. The method of claim 35 wherein the stent is adapted to exhibit a percent reduction in axial length of between 10% to 30% without fracture formation when placed under an axial load.

39. A method of fabricating a stent from a dip-coated polymeric substrate, comprising:
immersing a mandrel into at least a first polymeric solution having an inherent viscosity of about 4.3 to about 8.4 dl/g such that at least a first layer of a biocompatible polymer substrate is formed upon the mandrel and has a first diameter defined by the mandrel;
subjecting the substrate to a first elevated temperature at or above a glass transition temperature of the substrate; and
cooling the substrate actively to a second temperature lower than the glass transition temperature such that the substrate transitions to a glass state and imparts a shape memory effect;
processing the polymeric substrate to form an expandable stent scaffold configured for delivery and deployment within a vessel; and
reducing the first diameter of the stent scaffold to a second smaller diameter, wherein the stent scaffold retains one or more mechanical properties of the polymer resin such that the stent scaffold exhibits ductility upon application of a load.

40. The method of claim 39 wherein prior to forming an expandable stent scaffold, further comprising:
controlling a number of immersions of the mandrel into the first polymeric solution;
controlling a duration of time of each immersion of the mandrel;
controlling a delay time between each immersion of the mandrel.

41. The method of claim 40 further comprising controlling a withdrawal rate of the mandrel from the first polymeric solution after each immersion.

42. The method of claim 39 wherein the first polymeric solution comprises a polymer having a relatively high molecular weight.

43. The method of claim 39 wherein immersing a mandrel comprises further immersing the mandrel into a second polymeric solution such that a second layer of polymer is formed upon the first layer.

44. The method of claim 43 wherein the second polymeric solution comprises a drug or agent selected from the group consisting of antipoliferative, antineoplastic, antigenic, anti-inflammatory, antirestenotic, antilipid, antimitotics, metalloproteinase inhibators, and anti-sclerosing agents.

45. The method of claim 43 wherein the second polymeric solution comprises a radio-opaque material.

46. The method of claim 45 wherein the mandrel is immersed at one or both ends of the substrate into the radio-opaque material.

47. The method of claim 43 wherein the second polymeric solution comprises a $BaSO_4$ solution.

48. The method of claim 40 wherein controlling a number of immersions comprises immersing the mandrel between 2 and 20 times.

49. The method of claim 40 wherein controlling a duration of time comprises immersing the mandrel between 15 seconds and 240 minutes.

50. The method of claim 40 wherein controlling a delay time comprises delaying immersion of the mandrel between 15 seconds and 60 minutes.

51. The method of claim 39 wherein immersing a mandrel comprises inserting the mandrel into the first polymeric solution at a rate of 5 mm/min to 1000 mm/min.

52. The method of claim 39 further comprising applying a force within a lumen defined through the polymeric substrate such that the substrate expands from a first diameter to a second larger diameter.

53. The method of claim 52 wherein applying a force comprises introducing a pressurized gas within the lumen.

54. The method of claim 52 further comprising constraining expansion of the polymeric substrate via a molding tube.

55. The method of claim 54 further comprising expanding at least a portion of the polymeric substrate into a shape defined by the molding tube.

56. The method of claim 52 further comprising applying heat to the polymeric substrate while applying the force.

57. The method of claim 39 further comprising rotating the mandrel while applying heat.

58. The method of claim 39 further comprising controlling an angle of the mandrel relative to the polymeric solution.

59. The method of claim 58 wherein controlling an angle comprises alternating an angle of the mandrel up to 180°.

60. The method of claim 39 wherein the substrate has a length of 1 cm to 40 cm.

61. The method of claim 39 further comprising controlling a relative humidity of less than 30%.

62. The method of claim 39 further comprising controlling a temperature of the polymeric solution to be below a boiling point of a solvent contained within the polymeric solution.

63. The method of claim 39 further comprising mold-transferring one or more patterns from an outer surface of the mandrel to an inner surface of the substrate.

64. The method of claim 39 further comprising controlling a crystallinity percentage of the substrate.

65. The method of claim 39 further comprising drying the substrate at a glass transition temperature of the polymeric solution.

66. The method of claim 39 wherein subjecting the substrate to a first elevated temperature comprises subjecting the substrate to the first elevated temperature above the glass transition temperature of the substrate while reducing the first diameter.

67. The method of claim 66 wherein reducing comprises reducing the first diameter ranging from 3 mm to 9 mm to the second diameter ranging from 1.5 mm to 5 mm.

68. The method of claim 66 wherein cooling comprises reducing the substrate temperature to the second temperature of 20° C. below the glass transition temperature.

69. The method of claim 66 wherein the substrate formed upon the mandrel exhibits a percent elongation of between 10% to 300% at failure when placed under a 100 N to 300 N load.

70. The method of claim 66 wherein processing the polymeric substrate comprises laser machining or mechanical machining.

71. The method of claim 66 wherein the stent exhibits a percent reduction in diameter of between 5% to 70% without fracture formation when placed under a compressive load.

72. The method of claim 66 further comprising expanding a diameter of the stent via an expandable balloon by 5% to 70% without fracture formation.

73. The method of claim 66 wherein the stent is adapted to curve up to 180° about a 1 cm curvature radius without fracture formation.

74. The method of claim 66 wherein the stent is adapted to exhibit a percent reduction in axial length of between 10% to 30% without fracture formation when placed under an axial load.

* * * * *

UNITED STATES PATENT AND TRADEMARK OFFICE
CERTIFICATE OF CORRECTION

| | | |
|---|---|---|
| PATENT NO. | : 8,206,635 B2 | |
| APPLICATION NO. | : 12/143659 | |
| DATED | : June 26, 2012 | |
| INVENTOR(S) | : Kamal Ramzipoor et al. | |

It is certified that error appears in the above-identified patent and that said Letters Patent is hereby corrected as shown below:

In column 3, line 23, please replace "portion of cast cylinder" with --portion of the cast cylinder--.

In column 3, line 29, please replace "device" with --devices--.

In column 6, line 29, please replace "deposition The" with --deposition. The--.

In column 6, line 34, please replace "20° C. below" with --20° C below--.

Signed and Sealed this
Sixteenth Day of October, 2012

David J. Kappos
*Director of the United States Patent and Trademark Office*